United States Patent
Simons

(10) Patent No.: US 8,672,868 B2
(45) Date of Patent: Mar. 18, 2014

(54) METHOD AND APPARATUS FOR MONITORING AND OPTIMIZING BLOOD CIRCULATION GENERATED BY A PUMP

(75) Inventor: Antoine P. Simons, Maastricht (NL)

(73) Assignee: Maquet Cardiopulmonary AG, Hirrlingen (DE)

( * ) Notice: Subject to any disclaimer, the term of this patent is extended or adjusted under 35 U.S.C. 154(b) by 990 days.

(21) Appl. No.: 12/526,401

(22) PCT Filed: Feb. 7, 2008

(86) PCT No.: PCT/EP2008/000927
§ 371 (c)(1),
(2), (4) Date: Aug. 7, 2009

(87) PCT Pub. No.: WO2008/095699
PCT Pub. Date: Aug. 14, 2008

(65) Prior Publication Data
US 2010/0042259 A1 Feb. 18, 2010

(30) Foreign Application Priority Data

Feb. 9, 2007 (DE) .......................... 10 2007 007 198

(51) Int. Cl.
*A61M 35/00* (2006.01)
(52) U.S. Cl.
USPC .................. 604/4.01; 604/9; 604/33; 604/28; 604/509; 600/17; 600/18; 414/356; 414/477.2; 414/439
(58) Field of Classification Search
USPC .................................. 604/4.01, 9, 33, 28, 67
See application file for complete search history.

(56) References Cited

U.S. PATENT DOCUMENTS 6,066,086 A    5/2000   Antaki et al.

FOREIGN PATENT DOCUMENTS

| DE | 601 07 401 | 11/2005 |
| EP | 1 354606 A1 * | 4/2003 |
| EP | 1 354 606 | 10/2003 |
| JP | 2005066013 A | 3/2005 |
| JP | 3864944 B2 | 1/2007 |
| WO | 01/72352 | 10/2001 |

OTHER PUBLICATIONS

L.A. Baloa et al: "Control of Rotary Heart Assis Devices" Proceedings of 2000 American Control Conference (ACC 2000) Jun. 28-30, 2000 Chicago, IL, USA, BD. 5, 28. June 28, 2000. pp. 2982-2986, XP002487700.
Vollkron et al: "Advanced Suction Detection for an Axial Flow Pump." Artificial Organs, Sep. 2006, p. 665-670, XP 002487701, ISSN: 0160-564X.
Office Action for Japanese Patent Application No. 2009-551108, dated Jun. 25, 2013.

* cited by examiner

*Primary Examiner* — Tatyana Zalukaeva
*Assistant Examiner* — Ilya Treyger

(57) ABSTRACT

In a method for the automatic control of blood pumps, an optimization of the blood flow is achieved by periodic speed interventions and flow changes thereby occurring, using a formed differential variable and a control algorithm. In addition, the location of possible flow resistances on the venous or arterial side can be ascertained.

18 Claims, 3 Drawing Sheets

METHOD AND APPARATUS FOR MONITORING AND OPTIMIZING BLOOD CIRCULATION GENERATED BY A PUMP

RELATED APPLICATIONS

This application is a National Stage Entry (under 35 U.S.C. 371) of PCT/EP2008/000927 filed Feb. 7, 2008 which claims the benefit of priority to German Application No. 10 2007 007 198.3 filed Feb. 9, 2007, the disclosures of which are hereby incorporated by reference in their entirety.

The present invention relates to a method for monitoring and optimizing automatically the blood flow of a pump. Conclusions can be drawn from the control parameters as to the patient's condition and any problems in the blood circulation generated by the pump. This ensures that a sufficient blood flow takes place at all times.

The invention also relates to a medical apparatus which comprises a pump control system according to this method.

Blood pumps and associated control systems have long been known in the prior art. The task of blood pumps in combination with associated control systems is to ensure blood circulation intra- or extra-corporeally and thus to support or replace the pumping function of the patient's heart. Such blood pumps are used for a limited time to replace the heart function during operations on the heart or to support the heart function as a possible means for recovery of the weak heart in an extracorporeal circuit. Apart from the blood pump, use may be made, depending on the requirements, of all products commonly used for the extracorporeal circuit, such as for example cannulas, catheters, tubes and connectors, reservoirs, oxygenators, heat exchangers, blood concentrators and dialysers, bubble traps and filters.

Moreover, applications of heart support for an unlimited time and also artificial hearts are known, implantation of the pump taking place in these cases.

In all these applications of blood pumps, it is of utmost importance to generate reliably a sufficient blood flow by means of the pump. Especially in the case of the longer-term use of the blood pump, it is not possible manually to monitor and, if need be, correct the blood flow and associated parameters such as venous or arterial blood pressure or gas flow and gas mixture with the simultaneous use of oxygenators.

A reliable automatic control of the blood pump is therefore required especially for the use of ECMO (extracorporeal membrane oxygenation) or ELS (extracorporeal life support), since these applications take place over a fairly lengthy period of days up to weeks and also outside the operating theatre and without staff-intensive monitoring. But even in the case of applications in heart surgery, an automatic pump control offers greater convenience in handling and greater safety in the case of flow disruptions. Moreover, such a control is also conceivable in the case of implantable support systems (ventricular assist devices, VAD's) or in the case of an implantable artificial heart.

In the following, the factors are dealt with that adversely affect a desired blood flow, so that the pump settings and possibly additional parameters have to be changed.

For the venous blood return flow, it is known from practice and from Baloa et al., Vollkron et al. that, in the case of insufficient venous return flow of the blood, the large venous vessels and/or the atrium of the heart (depending on which one is being drained, the left or the right atrium) may collapse and then no blood flow at all or only an insufficient blood flow is possible. This venous return flow depends, amongst other things, on the filling status and the position and construction of the venous catheter. In the case of an excessively small filling status or in the event of contact of the catheter opening with the vessel wall, the vessel collapses and obstructs the venous and therefore the whole blood flow. This phenomenon is known in connection with centrifugal pumps, but can occur independently of the pumping principle. Furthermore, impairments of the venous return flow due to thromboses or suchlike or kinking of the tube in the venous line are conceivable. If such a state of insufficient venous return flow is reached, not only insufficient blood flow but also damage to the blood can occur due to cavitation and formation of gas bubbles. This life-threatening and patient-endangering state therefore has to be reliably avoided.

The monitoring of the pressure on the venous line is not sufficient to avoid collapse, because negative pressures can occur both in the case of collapse as well as in the operationally safe state. Moreover, the pressure on the venous side of the blood pump is to a large extent dependent on its position in relation to the patient (hydrostatic pressure) and can therefore be influenced thereby.

Furthermore, a collapse that has already occurred can at best be detected in this way and the tendency towards collapse can only be detected with difficulty.

In the arterial line, it is exclusively obstructions or closures due for example to thromboses or embolisms or kinking of the tube that are conceivable as an impairment of the blood flow. The problem of the collapse of the vessel wall does not exist on account of the arterial pressure. The level of the arterial pressure alone is not suitable as a measure for the detection of flow disruptions, because a high arterial flow resistance can be caused by the stated flow obstructions in the arterial line or by a high vascular resistance.

Approaches are disclosed in the prior art which characterize this problem mathematically. Baloa et al. disclose for example the method of forming the differential variable DRI (diminishing return index) DRI=dQ/dω by gradually increasing the pump speed, measuring the respective flow and differentiating by the pump speed. In the ideal case of unobstructed flow, this variable is a constant. With an incipient collapse, DRI becomes smaller, reaching the value 0 when collapse occurs. It is not however disclosed how a possible collapse is to be avoided or how a collapse that already exists is to be removed.

The method employed in many VAD's on the market of simply switching off the pump for several seconds in such cases appears to involve a high degree of risk due to the sudden total removal of the pump function and therefore the circulation support. In this case, the weakened patient's heart suddenly has to take over the whole burden of the blood circulation without a process of adaptation, and this can lead to it being overloaded and therefore to additional damage. In addition, the collapse can reoccur at any time with the described consequences when the original speed is restored. If, for the sake of safety, a lower pump speed is instead preset, the smaller flow thereby generated can possibly be maintained in a stable manner. Then, however, there is a reduced flow compared to the basic setting, said flow not being able to produce the full intended circulation support. In addition, the application described by Baloa et al. is used in a VAD, wherein it is not a vessel, but rather the atrium that collapses.

Vollkron et al. ascertain the venous return flow with the aid of the pulsatility in the flow signal, which is only present with a beating heart. In the case of an excessively high pump speed, the latter is reduced slowly down to a minimum, after which the speed is slowly increased again up to a maximum safe and desired flow. This slow decrease and increase, however, requires a certain period of time in which the pump seeks the optimum flow, but during which the optimum support is not guaranteed.

Against this background, the problem underlying the present invention is to make available a method for automatically regulating and optimizing, within the range of the desired preset values, the blood flow from blood pumps whilst avoiding life-threatening states, wherein the method is intended to be universally usable, i.e. one that functions reliably even in the event of cardiac arrest, and in the case of corrected impairments of the blood flow it should be possible to detect their location in the circulation, venous or arterial, in order to permit rapid measures to be taken in a targeted manner.

This problem is completely solved by the method according to the invention and a device for performing the method.

This new method can automatically perform periodic interventions into the pump speed, wherein differential variables are ascertained by determining the effect on the flow by recording the measured values of pump parameters such as the speed and the blood flow per unit of time and their relationship with one another, said differential variables characterising the flow states and being suitable for detecting and removing return flow disruptions and for analyzing the state of the heart.

The blood flow required depending on the patient's needs is established in a known manner by the doctor in charge or perfusionist and the numerical magnitude "¾ of the blood flow required in the circulation" required for the method according to the invention is thus also known. For example, the required blood flow can be calculated using the du Bois formula for a patient-related body area, cardiac indices in the range of 2.5-4 $l\ min^{-1}\ m^{-2}$ being normal.

In contrast to Baloa et al., the pump speed is not only increased, but also decreased and the changed blood flow is measured. In this way, if a tendency towards collapse is detected, it is possible by reducing the pump speed to achieve a sufficient venous return flow again with regeneration of the incipient collapse. Thereafter, the speed and the flow can be optimized gradually by increasing the speed and measuring the changed flow (blood flow), stable values above the initial value for incipient collapse being able to be achieved.

The method according to the invention, wherein an incipient collapse is not only detected, but also rapidly eliminated and the flow thereafter optimized, differs markedly from the prior art (Baloa et al., Vollkron et al.), where differential values are also ascertained, but no solution is disclosed for the regeneration of an incipient or existing collapse. The method employed in many VAD's on the market of simply switching off the pump for several seconds in such cases appears to involve a high degree of risk due to the sudden total removal of the pump function and therefore the circulation support. In this case, the weakened patient's heart suddenly has to take over the whole burden of the blood circulation without a process of adaptation, and this can lead to it being overloaded and therefore to additional damage.

On the other hand, the removal of the collapse disclosed by Vollkron et al. requires a certain amount of time until the pump speed has been reduced, and then also increased again. In particular, the principle according to the invention is distinguished here by a rapid slowing-down of the pump with a subsequent increase in the pump speed, this function also being present with a non-pulsatile blood flow, e.g. in the case of cardiac arrest.

The method according to the invention and a device with which the method according to the invention can be performed is described with the aid of the following figures in the drawing.

Figure 1:
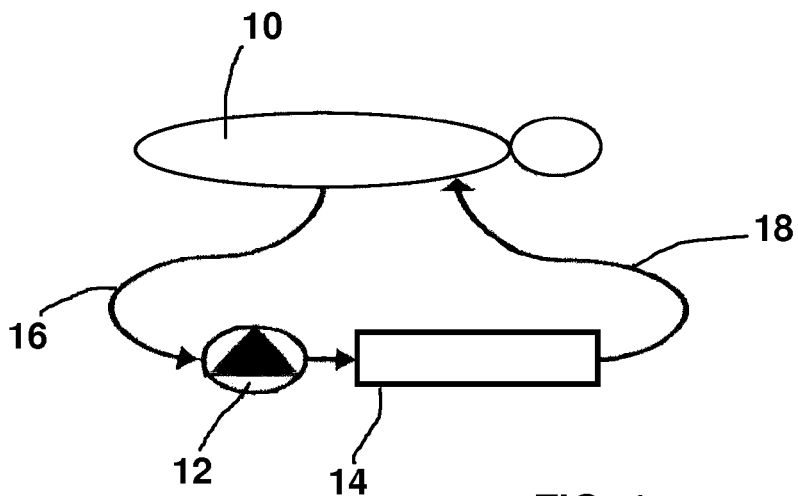
FIG. 1 shows a diagram of a minimized extracorporeal bypass with a pump, oxygenator and hose lines.

In FIG. 1, a patient is indicated by 10, who is connected to an extracorporeal blood circuit, comprising a pump 12, an oxygenator 14, a venous hose line 16 and an arterial hose line 18.

During the initial phase of a minimized closed extracorporeal circuit system (FIG. 1), the pump speed (PS) is gradually increased by α rev/min. The value "differential flow speed ratio" (DFSR) is constantly calculated via $\Delta_{flow}/\Delta_{speed}$ (=Δflow/ΔPS [l/min.] [revolutions/min]) until ¾ of the required flow is reached. The mean value of the calculated differential represents an approximate value of the flow/speed ratio for each individual patient with circulation support. This value is halved and used as threshold value T (defined). During the bypass, the pump speed (pump speed, PS) is reduced by β rev/min for ε seconds. Following the pump speed reduction (dPS), the flow change (dF) is calculated and the differential variable "differential flow speed ratio" (DFSR), i.e. Δflow/ΔPS, is ascertained therefrom.

DFSR≤1T signifies an excessive drainage, i.e. an excessively small return flow, and requires a sudden regulation of pump speed PS down to 50% of the initial pump speed. After γ seconds, PS gradually increases by δ rev/min up to 95% of initial pump speed PS. DFSR>2T signifies an excessively small drainage, which requires an increase in pump speed PS by ε rev/min. The calculation of the new DFSR shows the success of the return flow optimization.

The value of 1.5T is taken as the upper threshold value. DFSR>1.5T indicates that a higher pump speed and therefore also a higher flow is possible. When the option is activated, DFSR>1.5T can cause the pump to increase the speed by ζ rev/min. The calculation of the new DFSR shows the success of the return flow optimization. If it is desired to avoid a possible over-perfusion, a maximum flow can be inputted, which then receives priority over the speed increase.

A diagram of the control unit described above is illustrated in FIGS. 2 and 3. FIG. 4 shows results of a practical application.

Figure 2:
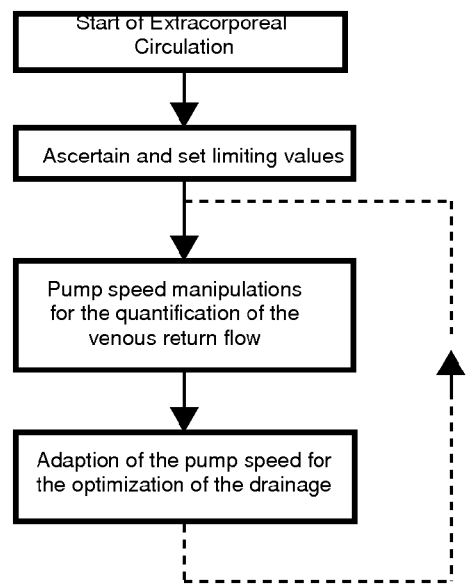
FIG. 2 shows a flow diagram with the illustration of the main steps of the algorithm.

FIG. 2 shows, in a flow diagram, the inventive procedure (algorithm) for achieving an optimum drainage. After the start of the extracorporeal blood circulation, the necessary patient-related limiting values are ascertained, as described by way of example in respect of FIG. 1. The venous blood return flow is then quantified via a change in the pumping capacity and the pumping capacity enabling optimum drainage is ascertained therefrom and set.

Figure 3:
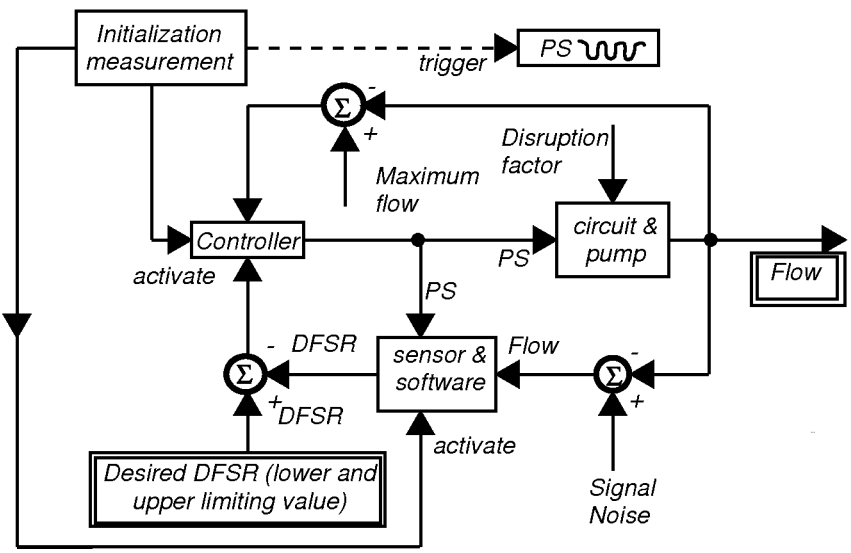
FIG. 3 shows a diagram of a control circuit according to the invention, wherein the setpoint value is a range of permitted values of the differential flow speed ratio (DFSR), which allows the control system to control the pump speed (PS) and accordingly generates a flow, a maximum flow also being able to influence the DFSR control, i.e. to prevent an over-perfusion.
Figure 4:
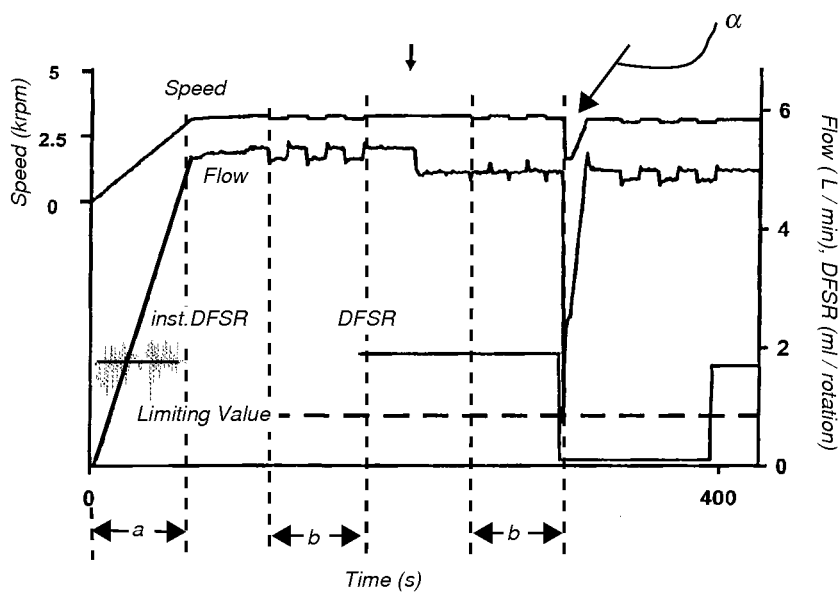
FIG. 4 shows a graphic relationship between changed pumping capacity and ascertained DFSR values.

FIG. 3 represents a control circuit according to the invention, which constantly ascertains, via desired DFSR values, new DFSR actual values from the instantaneous flow of the pump speed, matches the DFSR actual values with the desired DFSR values and from this constantly resets the pump speed in order to prevent both an excessive drainage as well as a drainage that is too small.

FIG. 4 illustrates how a mean value is formed (inst. DFSR) after increasing the pump speed and simultaneously measuring the DFSR. Half of this value is set as a limiting value. After the DFSR has been ascertained, the venous return flow is reduced (represented by the arrow). A subsequent measurement to ascertain the DFSR ascertains a reduction of the same, after which the pump speed is effectively slowed down to 95% by means of a 2-step reduction. A subsequent measurement of the DFSR clearly shows an increase in this value and an optimization of the drainage, i.e. adaptation of the pump speed to the available venous flow.

Furthermore, process steps a and b from process claim 1 as originally filed are entered in FIG. 4, process step d being indicated by a further arrow.

Return flow obstructions increase the flow resistance on the inlet side of the pump, and this reduces the pump preload and adversely affects the pump flow. In the case of clotting of an oxygenator, the resistance is similarly increased, but this additional resistance then occurs after the pump. Both cases influence the DFSR, but in order to distinguish between clotting of the oxygenator and obstruction of the venous return flow to the pump, the additional measurement of the drop in pressure across the oxygenator (pressure at inlet−pressure at outlet) can provide the required information. If the DFSR falls, the level of the differential pressure on the oxygenator indicates the cause of the increased resistance, i.e. whether it is before or after the pump. If the differential pressure is small, an obstruction of the venous return flow is present, if the differential pressure is high, clotting of the oxygenator has occurred.

Furthermore, the measurement of the DFSR provides information concerning the pumping capacity of the heart, in particular the right chamber of the heart. In the case of a recovering heart or a mean pumping speed thereby reduced, the DFSR should not change. The recovering heart reacts, according to the Frank Starling mechanism, to the increased preload and tries to achieve the required output capacity. The venous and arterial pressure, and therefore the DFSR, thus remain constant. In the case of an insufficient and only partially recovered heart, a reduction in the mean pump speed leads to an increase in the DFSR. The insufficient heart is not capable of overcoming the increased preload when the pump support is reduced. In this case, therefore, the venous pressure increases and the arterial pressure diminishes. The body in turn reacts to the falling arterial pressure with vasoconstriction, in order to compensate for a further drop in the arterial pressure. The preload of the pump increases as a result, whilst the after-load remains approximately constant: the DFSR increases.

The reaction to speed-reducing control steps can be used, in combination with a flow pattern analysis, to ascertain the heart status. The beating heart influences the flow pattern of a supporting centrifugal pump, in such a way that the aortic pressure increases during systole, and the flow via the pump thereby diminishes. If the mean pump speed is reduced and speed-reducing control steps then follow, the following pulses of the flow signal provide valuable information concerning the heart status and its pumping reserve. After reduction of the support, the gradient and the amplitude of the flow pulses provide direct information concerning the contraction capacity and therefore the regeneration of the heart.

The above methods can be used to determine the heart status and the reserves of the pumping capacity, and can be used in an appropriate way to wean the patient off the heart support. They can be used in a very helpful way as a tool for heart monitoring, while the latter receives more preload via the periodic speed reductions and is thereby trained.

Another possibility for ascertaining the heart status and heart regeneration is to determine the time that the heart requires to compensate for abrupt pump support and to deliver the total flow required by the body, consisting of pump flow and cardiac output.

The Frank Starling mechanism is used directly in both methods. However, this application requires, in contrast to the non-invasive determination of the DFSR, an invasive measurement of the arterial and venous blood pressure.

In this way, it is also possible to automate the monitoring and the optimization of the blood flow, this being necessary for heart support and regeneration in the case of a long-term application. Moreover, indications can be obtained concerning the recovery of the heart through the reaction of the heart to a changed blood flow via the pump. The higher the pulsation in the arterial blood pressure with a reduction in the pumping capacity, the greater the capacity and therefore the recovery of the heart. The required support can therefore be given automatically during the time of the heart support, the pump automatically being able to assume a greater share of the pumping capacity in the event of a reduction of the pumping capacity of the heart. A risk-free regeneration of the heart and thereafter automatic continuous weaning off from the pump is thus possible.

Figure 5:
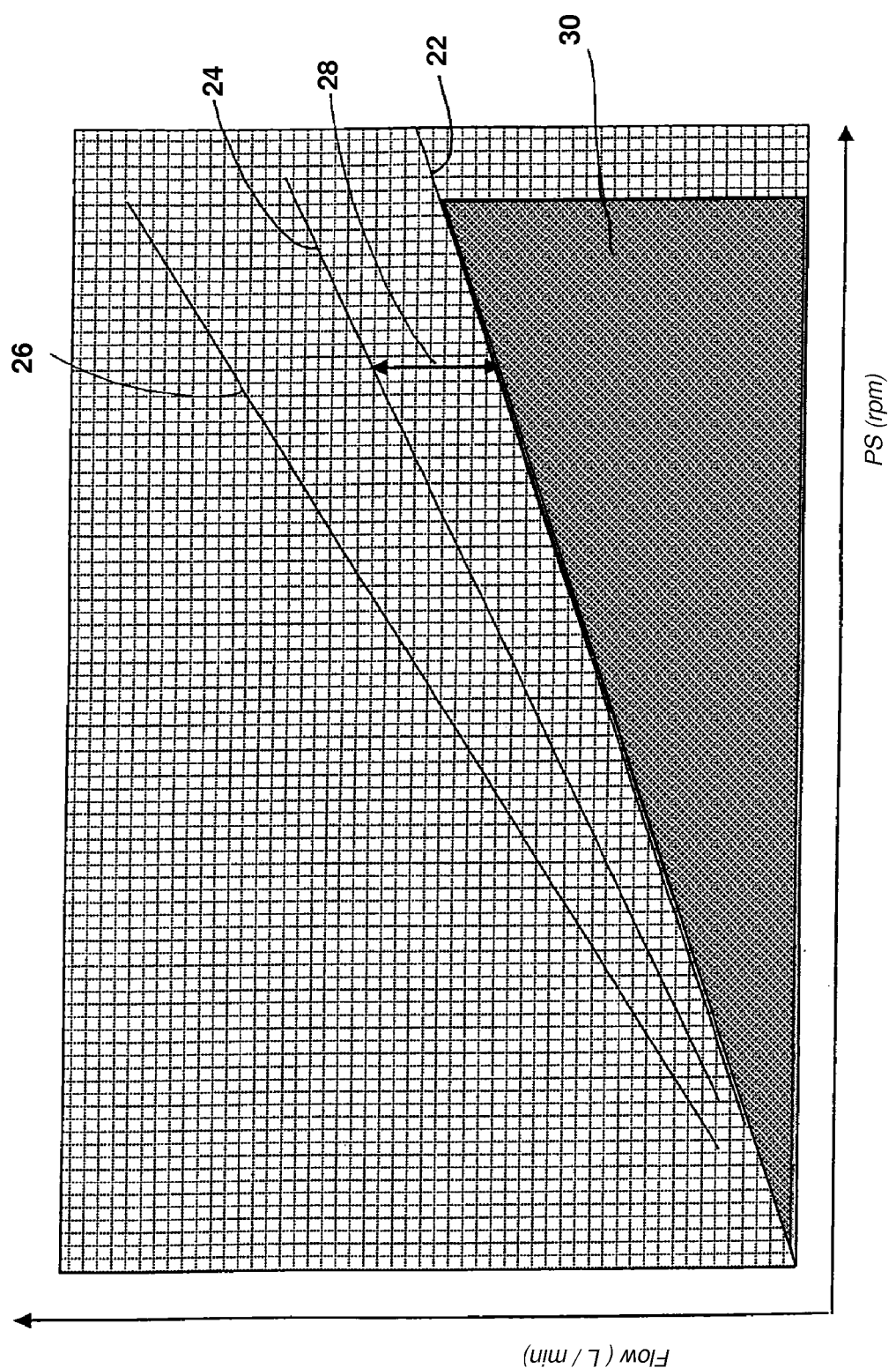
FIG. 5 shows a control sequence represented in an illustration, such as can preferably take place according to the invention.

FIG. 5 shows, by way of example, how a control according to the invention can take place. After the required blood flow has been ascertained, this being a procedure familiar to the person skilled in the art addressed here, the control procedure commences and ascertains the DFSR. A fraction thereof, in the example here half thereof, is defined in the manner described as threshold value T.

In FIG. 5, the straight line for DFSR=1T is represented with 22. The course of DFSR=1.5T is shown with reference number 24 and DFSR=2T with 26. Operational area 28 of the method according to the invention is indicated between straight lines 22 and 24. Below straight line 22 (DFSR=1T), the undesired operational area is marked as grey area 30 (DFSR<1T), in which partial or complete collapse can occur. This area is critical for the patient's safety and it is therefore absolutely essential for it to be reliably avoided.

When DFSR≥1.5T, the pump speed is increased, when DFSR≤1T, it is reduced (and thereafter increased again). A stable operation in the operational area between 1T and 1.5T is thus achieved.

The starting points of straight lines DFSR=1T, DFSR=1.5T and DFSR=2T do not begin at the origin in the above exemplary diagram. It goes without saying that, depending on the existing pressure conditions during use with a centrifugal pump mentioned by way of example, a positive flow >0 generated by this pump cannot be brought about until a given speed PS and the determination of DFSR cannot therefore begin until this speed and ends at ¾ of the desired flow. The values for the speed (PS) occurring in the pump circuit and flow >0 up to ¾ of the desired flow generated by the pump (=positive) thus have to be evaluated in order to ascertain the DFSR and thus T.

For a general understanding, reference is once again made to the fact that the DFSR is formed via the variables Δflow/Δspeed for a sequence of different speeds. This value, however, is therefore to be understood as a differential variable. The DFSR therefore represents the $1^{st}$ derivative (gradient of the function Δflow/Δspeed at each point) of the respective function.

For unchanging return flow conditions, i.e. with an almost ideal, unobstructed blood flow, a straight line is to be expected for this function and a constant DFSR variable as a derivative thereof. This behaviour is used to ascertain the inst. DFSR and thus threshold value T.

A change in this gradient, equivalent to a changed value for the DFSR in the considered range of the pump speed, indicates a change in the flow conditions.

In the method according to the invention, periodic speed interventions are carried out from a given pump speed and the differential variable DFSR for the region of this intervention is formed from Δflow/Δspeed for the upper and lower considered speeds of the intervention.

By means of a comparison with threshold value I (fraction of inst. DFSR, in the special case ½ inst. DFSR), the pump speed is regulated in such a way that flow conditions are kept within a preset range for the DFSR. This preset range from T to 1.5T characterizes, in this example of embodiment, pump speeds adapted to the available return flow volume, overdrainage being avoided on the one hand and the predetermined required blood flow under valuable drainage conditions being achieved to the best possible effect on the other hand.

It does not therefore concern a control procedure for the blood flow in general, but rather the adaptation of the pump speed to the flow conditions with a predetermined target value for the maximum blood flow.

In a development of this method, the gas supply of an oxygenator present in the blood circuit can be integrated into the control circuit. Since the blood flow is adjusted variably by regulating the pump, the gas flow and the oxygen content of the gas flow must also be automatically adapted to the given blood flow and the patient's needs. For this purpose, it is proposed to use the existing blood flow and the partial pressures of blood gases $pO_2$ and $pCO_2$ measured online to regulate the gas supply. If both partial pressures are normal, the gas mixture and the gas flow can be maintained. If $pO_2$ is too small, the oxygen content of the supplied gas mixture must be automatically increased and vice versa. An excessively high value of $pCO_2$, on the other hand, is adjusted by an increase in the gas flow, whilst an excessively low value of $pCO_2$ is adjusted by reducing the gas flow. The algorithm can, analogous to that proposed for the blood flow, be constituted with threshold or limiting values.

In this case, the automatic detection of the differential pressure on the oxygenator and a warning signal when a threshold value is reached for the differential pressure or gas partial pressures is of particular importance. The risk of an incipient under-supply to the patient for heart and lung function can thus be detected and removed by suitable measures, such as for example replacement of a clotted oxygenator.

Although only measured values of centrifugal pumps have been disclosed in FIG. 4, it is evident to the person skilled in the art that the problem of the venous return flow and the risk of the collapse of vessels or ventricles can in principle occur with the use of blood pumps employing any functional mode and can be solved according to the invention.

It goes without saying that, with the above non-invasive methods, not only the indicated flow of the pump can be used as a parameter, but also the variables of the pump proportional to this flow, such as for example the power or current consumption of a centrifugal pump or the current or the power consumption of active magnetic bearings of axial pumps, can be used as control parameters, without departing from the scope of the invention.

In a method for the automatic control of blood pumps, an optimization of the blood flow is achieved by periodic speed interventions and flow changes thereby occurring, using a formed differential variable and a control algorithm. In addition, the location of possible flow resistances on the venous or arterial side can be ascertained A method for controlling blood pumps, characterized in that the differential variable "differential flow speed ratio" (DFSR) is formed according to $\Delta_{delivery\ capacity}/\Delta_{speed/pump\ speed}$ by automatic periodic speed changes or pump speed changes and the change in the delivery capacity of the pump measured for this, the level and course of said differential flow speed ratio being used in an algorithm which brings about the optimization of the blood flow.

A method characterized in that the automatic periodic speed or pump speed changes can be both increases and decreases.

A method characterized in that the change in the delivery capacity is determined by a change in pump parameters.

A method characterized in that the determination of the speed or pump speed changes and the change in the delivery capacity of the pump measured for this take place non-invasively.

A method characterized in that the determination of at least one parameter takes place invasively.

A medical apparatus which contains a pump for delivering blood with a control system.

The invention claimed is:

1. A method for operating blood pumps of an intra- or extra-corporeal blood pump circuit with the following process steps:
   a) determining a threshold value T from differential flow speed ratio variables of blood flowing through the blood pump circuit (DFSR variables), wherein individual DFSR variables are calculated from a quotient of a differential blood delivery capacity with respect to a corresponding differential blood pump speed, wherein the pump speed is gradually increased up to a value less than a predetermined blood flow of the blood pump circuit when the DFSR variables are obtained;
   b) subsequently reducing the blood pump speed and obtaining associated DFSR variables of blood flowing through the blood pump circuit while reducing the blood pump speed (determined DFSR variables);
   c) comparing the determined DFSR variables from process step b) with the threshold value T from process step a) in order to assess drainage flow of the blood pump circuit;
   d) changing the blood pump speed depending on whether the determined DFSR variables according to process step b) is greater than, equal to or less than the threshold value T to regulate blood flow through the blood pump circuit.

2. The method according to claim 1, characterized in that the threshold value T is half a mean value of the DFSR variables.

3. The method according to claim 1, characterized in that, when the determined DFSR variable≤1T, the blood pump speed is reduced and thereafter is increased over a defined period of time.

4. The method according to claim 1, characterized in that, when the determined DFSR variable≥2T, blood pump speed is increased.

5. A device for performing a method according to claim 1, characterized in that the blood pump circuit comprises a first means for detecting, calculating and comparing the determined DFSR variables and a second means for setting the blood pump speed as a function of a result from a comparison of the determined DFSR variables with the threshold values T.

6. A method for operating a blood pump of a blood circulation system to regulate blood flow comprising the steps of:
determining a minimum threshold value based on a differential flow speed ratio of blood flowing through the blood circulation system over a first period of time (DFSR);
comparing: (a) a determined differential flow speed ratio of blood flowing through the blood circulation system obtained over a second period of time when pump speed is decreased (determined DFSR) to (b) the minimum threshold value in order to assess drainage flow of the blood circulation system; and
adjusting the pump speed to regulate blood flow through the blood circulation system by first decreasing the pump speed to a non-zero magnitude and subsequently increasing the pump speed, wherein the step of adjusting occurs in the event the determined DFSR is less than the minimum threshold value.

7. The method of claim 6, wherein the step of adjusting the pump speed comprises decreasing the pump speed at a first rate of change to a non-zero magnitude and subsequently increasing the pump speed at a second rate of change, wherein the second rate of change is smaller than the first rate of change.

8. The method of claim 6, wherein the minimum threshold value is associated with a condition of impeded drainage; and wherein the step of adjusting the pump speed comprises decreasing the pump speed a sufficient amount to restore stable drainage of blood through a vessel and subsequently increasing the pump speed a sufficient amount to stabilize blood flow through the vessel.

9. The method of claim 8, wherein the step of adjusting the pump speed comprises minimizing or preventing backflow during the step of first decreasing pump speed to a non-zero magnitude.

10. The method of claim 6, wherein the step of increasing the pump speed comprises increasing pump speed to a magnitude less than a pump speed corresponding to a detection that the determined DFSR is less than the minimum threshold value.

11. The method of claim 6, wherein the step of adjusting pump speed comprises decreasing pump speed and subsequently increasing pump speed such that a corresponding differential flow speed ratio is greater than the determined DFSR.

12. The method of claim 6, wherein the step of regulating blood flow comprises decreasing pump speed down to 50% of a pump speed correlated to a detection that the determined DFSR is less than the minimum threshold value.

13. The method of claim 6, wherein the step of regulating blood flow comprises increasing pump speed up to 95% of a pump speed correlated to the detection that the determined DFSR is less than the minimum threshold value.

14. The method of claim 6, further comprising the steps of:
determining a maximum threshold value based on the DFSR;
comparing the determined DFSR to the maximum threshold value; and
increasing pump speed in the event the determined DFSR is greater than the maximum threshold value.

15. The method of claim 6, wherein the minimum threshold value is determined based on a mean DFSR obtained over the first period of time, wherein pump speed is increased during the first period of time.

16. The method of claim 15, wherein the minimum threshold value is the mean DFSR.

17. The method of claim 14, wherein the maximum threshold value is determined based on a mean DFSR obtained over the first period of time, wherein the pump speed is increased during the first period of time and wherein the maximum threshold value is $\geq 2$ times the mean DFSR.

18. The method of claim 6, further comprising the step of assessing cardiac pump capacity or cardiac recovery based on the step of comparing.

* * * * *